(12) United States Patent
Mathews et al.

(10) Patent No.: US 8,690,068 B2
(45) Date of Patent: Apr. 8, 2014

(54) MINIATURIZED UHF RFID TAG FOR IMPLANTABLE MEDICAL DEVICE

(75) Inventors: Michael Mathews, Olive Branch, MS (US); Chakravarty Tapas, Kolkata (IN); Steven Tethrake, Collierville, TN (US); Robin Turner, Memphis, TN (US); Kuldeep Tyagi, Ghaziabad (IN)

(73) Assignee: Warsaw Orthopedic, Inc., Warsaw, IN (US)

( * ) Notice: Subject to any disclaimer, the term of this patent is extended or adjusted under 35 U.S.C. 154(b) by 4 days.

(21) Appl. No.: 13/476,134

(22) Filed: May 21, 2012

(65) Prior Publication Data

US 2013/0306740 A1    Nov. 21, 2013

(51) Int. Cl.
*H01Q 1/38*    (2006.01)

(52) U.S. Cl.
USPC ........................................ 235/492; 340/572.7

(58) Field of Classification Search
USPC ........................................ 235/492; 340/572.7
See application file for complete search history.

(56) References Cited

U.S. PATENT DOCUMENTS

| | | | |
|---|---|---|---|
| 5,231,407 A * | 7/1993 | McGirr et al. | ......... 343/700 MS |
| 7,561,107 B2 | 7/2009 | Al-Mahdawi | |
| 7,750,813 B2 | 7/2010 | Deavours et al. | |
| 7,819,318 B2 | 10/2010 | White et al. | |
| 7,855,697 B2 | 12/2010 | Chamarti et al. | |
| 8,253,555 B2 | 8/2012 | Stevenson et al. | |
| 8,253,630 B2 | 8/2012 | Tu | |
| 8,462,052 B2 | 6/2013 | Yamagajo et al. | |
| 2005/0012667 A1 * | 1/2005 | Noujeim | ................ 343/700 MS |
| 2008/0062044 A1 | 3/2008 | Al-Mahdawi | |
| 2009/0096613 A1 * | 4/2009 | Westrick | .................... 340/572.7 |
| 2011/0001610 A1 | 1/2011 | Stevenson et al. | |
| 2011/0291836 A1 * | 12/2011 | Deavours et al. | .......... 340/572.7 |
| 2012/0154251 A1 | 6/2012 | Yung et al. | |
| 2013/0043316 A1 | 2/2013 | Liu | |

FOREIGN PATENT DOCUMENTS

| | | |
|---|---|---|
| WO | WO2007141505 | 12/2007 |
| WO | 2009027854 A1 | 3/2009 |
| WO | 2009049011 A1 | 4/2009 |
| WO | 2010042849 A1 | 4/2010 |

* cited by examiner

Primary Examiner — Daniel Hess

(57) ABSTRACT

This invention relates to a novel architecture of a passive RFID (Radio-Frequency Identification) tag which is highly miniature in size, capable of metal mounting and suitable for global operation in the entire UHF band (860 MHz to 960 MHz) without necessity of territory specific optimization of the antenna design layout.

This invention envisages a novel antenna design that consists of a circular or rectangular microstrip antenna of ultra-small size (~λ/50), which is suitably loaded in shunt by lumped components resistor (R), inductor (L) and capacitor (C). The feed point, feed layout and the loading values are so optimized that a single tag will display optimum performance in all the territories.

This invention relates to a method of encapsulating the passive tag with radio transparent materials like Radel® R, as well as a metal backplane so that the encapsulated tag can withstand autoclaving while maintaining the required performance.

18 Claims, 10 Drawing Sheets

RFID TAG V1
LAYER1 - PRIMARY SIDE

RFID TAG V1
LAYER2 - SECONDARY SIDE

RFID TAG V2
LAYER1 - PRIMARY SIDE

RFID TAG V2
LAYER2 - SECONDARY SIDE

MINIATURIZED UHF RFID TAG FOR IMPLANTABLE MEDICAL DEVICE

FIELD OF THE INVENTION

The present invention relates to radio frequency identification (RFID) tags that are particularly suitable for item location, identification, inventory and tracking applications in the medical device industry.

BACKGROUND OF THE INVENTION

An RFID system consists of a reader (sometimes called an interrogator) and a transponder (or tag), which usually has a microchip with an attached antenna. There are different types of RFID systems, but usually the reader sends out electromagnetic waves that the tag is designed to receive. Passive tags have no power source. Passive tags draw power from the field created by the reader and use the energy from the field to power the microchip's circuits. The chip then modulates the waves that the tag sends back to the reader. The reader then converts the new waves into digital data. Active tags have a power source and broadcast their signal. Active real time location systems don't respond to signals from the reader, but rather broadcast at set intervals. Which readers pick up those signals and software is used to calculate the tag's location.

Conventional RFID inventory management systems fail to provide fast and error-proof information in a timely manner, which creates inefficiencies. These inefficiencies have a qualitative and quantitative impact in the cost and timely management of hospitals and health care supply chains. The present invention improves the operation of current RFID technology which in turn improves the operational efficiency of hospitals and health care supply chains while reducing both inventory and labor costs.

RFID technology is helping improve the mobility of health care delivery. However, improvements in RFID technology can help provide better real time location systems, asset tracking, item tracking, human tracking, inventory management, recall management and expiration alerts. Application of RFID in the medical device industry is a growing field that is providing the best in care solutions to the patient and helping providers to achieve faster and more accurate results.

SUMMARY OF THE INVENTION

One object of the present invention is to provide a low profile RFID Tag. The invented RFID Tag provides a low profile device, wherein said low profile circuit board is about 11 mm or less in any unit dimension, or about 9 mm or less in any unit dimension, or about 7 mm or less in any unit dimension.

Another object of the present invention is to provide an RFID tag that that has universal application on many devices that can be modified to suit the specific space availability on the medical device. In one aspect of the invention a metal mount tag is included that can be used to mount the RFID Tag to medical implants, instrument, and the like.

Another object of the present invention is to provide a RFID Tag that is designed to include an integrated copper/metal foil cover such that the detuning effect of attachment to metallic materials is minimized or nullified altogether.

It is another objective of the invention to provide the RFID Tag with a metal/copper foil backing to the reading range.

Another object of the present invention is to provide RFID integrated circuits that include integrated circuits (IC), substrate, and lump components.

Another object of the present invention is to provide RFID integrated circuits that provide high chip performance that is EPC Global Class 1 Gen 2 compliant and provides a minimum of 884 Bit memory and a minimum of 512 Bit user memory.

Another object of the present invention is to provide a RFID tag that is environmentally resilient and is able to withstand environmental rigors like autoclaving heat.

Another object of the present invention is to provide an environmentally resistant RFID tag. In one aspect of the invention the RFID tag is encapsulated in a thermoplastic polymer such as Radel® R.

Another object of the present invention is to provide an RFID tag having a low profile antenna and components which outperform relatively larger antenna and components.

It is another objective of the invention to use shunt loading of a cavity backed microstrip antenna to reduce the size drastically while maintaining complex impedance match over the entire 860 MHz to 960 MHz frequency band.

It is another objective of the invention to optimize the lumped load values for RLC components—namely a resistor (R), inductor (L) and capacitor (C) so that the tag retains its projected performance over the entire UHF range.

Another object of the present invention is to provide a RFID tag that is operable within a 6"-12" read range that can be used with implants, instruments and other medical devices.

All the above features when taken singularly or in any subcombinations make this invention unique.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

In one aspect, the invention comprehends a new architecture for a UHF passive RFID Tag that includes an UCODE G2XM integrated circuits (IC) (obtainable from NXP Semiconductor) driving a small sized microstrip antenna loaded with lumped components for the principal objective of developing an Ultra-compact RFID tag for predominantly medical applications and having a read range of approximately 6-8 inches. The tag is then encapsulated in thermoplastic polymer like Radel® R with a miniature metal/copper foil backing thereby protecting the performance from harsh environment like autoclaving and proximity of metal items.

In the present invention the UHF tag consists of five major constituents namely UCODE G2XM integrated circuit (obtained from NXP Semiconductors), lumped passive components (e.g., resistor (R), inductor (L), and capacitor (C)), encapsulation, a thin metallic plane and a microstrip patch antenna with generally regular shape (e.g., circular, rectangular, or square). The present invention relates to the method of inter-relationship between two or more of these constituents in a manner that optimizes the passive tag performance in terms of reading range, impedance match and backscattering coefficient.

It is another objective of the invention to use shunt loading of cavity backed microstrip antenna to reduce the size drastically while maintaining complex impedance match over the entire 860 MHz to 960 MHz frequency band.

Figure 1A:
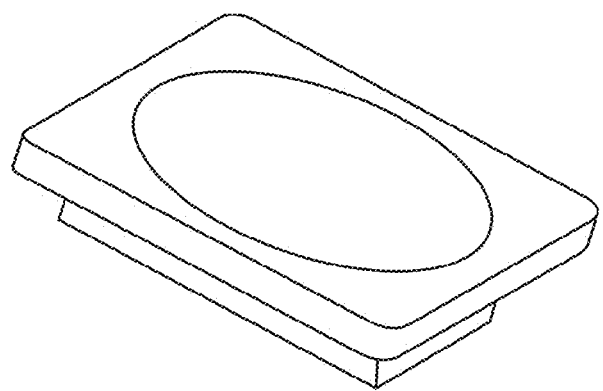
FIG. 1A—RFID Tag, Design 1
FIG. 1B—RFID Tag, Component Dimensions of Design 1
FIG. 2A—RFID Tag, Design 2
FIG. 2B—RFID Tag, Component Dimensions of Design 1
FIG. 3A—A Simplified Equivalent Circuit of Circular Microstrip antenna using generalized transmission line model.
Figure 1B:
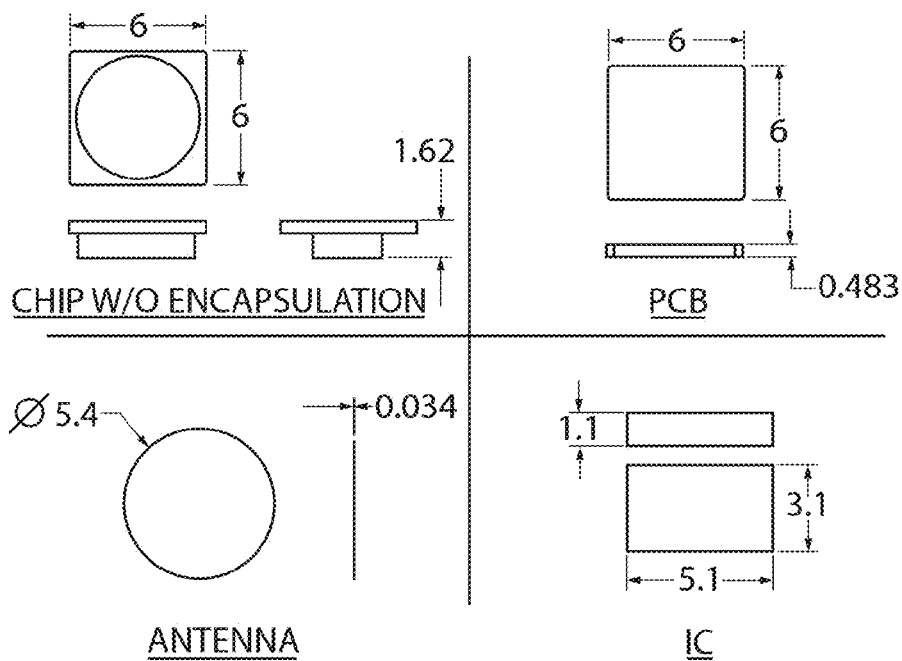

FIG. 1A—shows an enhanced view of the RFID Tag of Design 1. FIG. 1B—shows the component dimensions of Design 1 of the chip without encapsulation, the antenna, the PCB, and the chamber to housing the integrated circuit. The dimensions are presented in millimeters (mm).

Figure 2A:
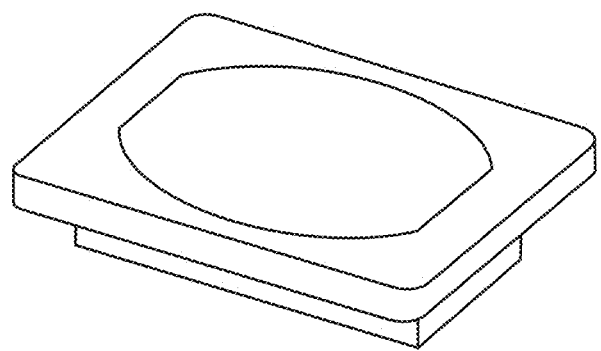
Figure 2B:
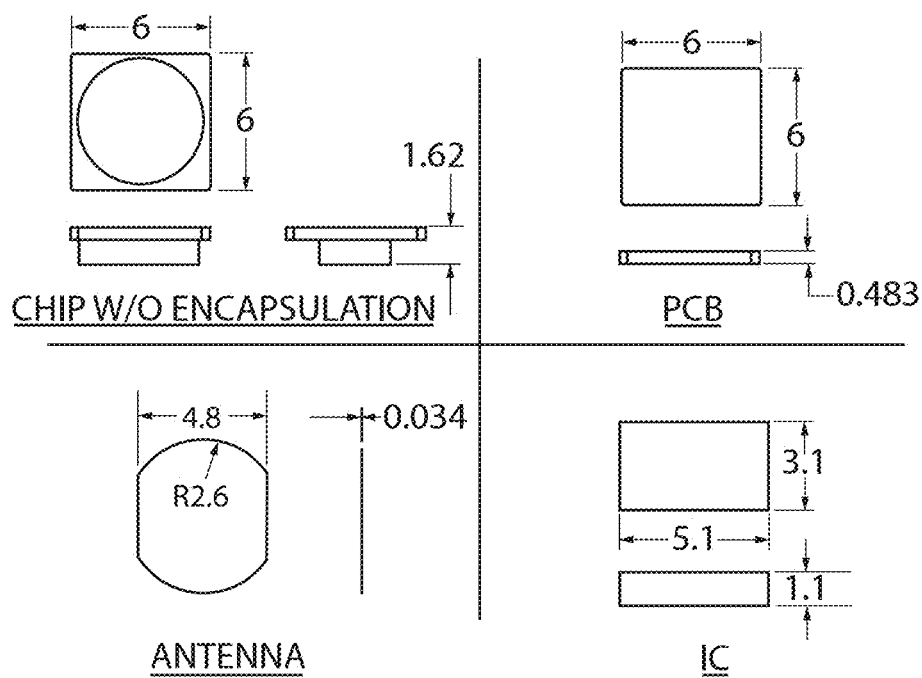

FIG. 2A—shows an enhanced view of the RFID Tag of Design 2. FIG. 2B—shows the component Dimensions of Design 2 of the chip without encapsulation, the antenna, the PCB, and the chamber housing the integrated circuit. The dimensions are presented in millimeters (mm).

Figure 3A:
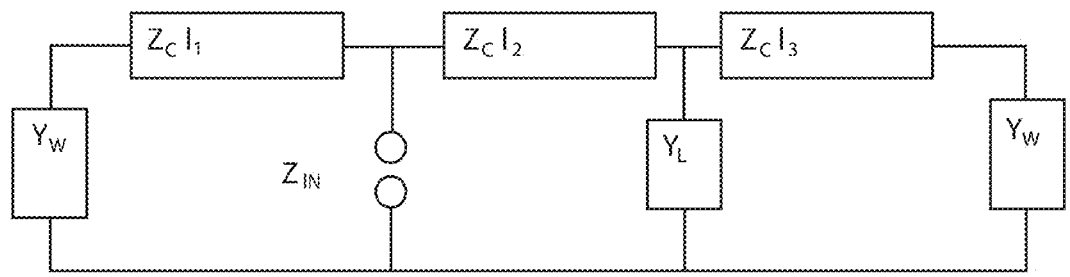
FIG. 3B—Typical load (YL) configuration using Passive Components.
FIG. 3C—Typical load configuration using Passive Components.
Figure 3B:
Figure 3C:
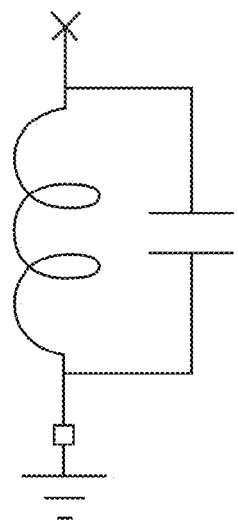

FIG. 3A displays a simplified generalized transmission line model of a circular Microstrip patch antenna. In FIG. 3A, $Y_W$ accounts for the wall admittance of the patch, $Z_{in}$ is the input impedance seen by the feed and $Y_L$ is the additional load in the form of lumped passive components. In its fundamental resonance, a circular microstrip patch can be considered as a parallel tuned circuit. Additional load admittance is used to lower the resonance frequency. FIG. 3B shows the typical load configuration using three passive components: an inductor, resistor and capacitor. However, since lowering of resonance frequency leads to a much smaller electrical volume, the radiation efficiency is affected. Also it is to be noted that the antenna needs a complex conjugate match with the RFID integrated circuit like UCODE G2XM as shown in FIG. 3C.

In the present invention, a planar antenna is printed on the top side of a thin microwave laminate and the integrated circuit is mounted below. The unbalanced (RF) port of the integrated circuit is electrically connected to the antenna using both the methods of probe feeding and proximity coupling. An optimized shape of ground pattern is printed on the bottom side and this is connected to the ground port of the integrated circuit. In this invention, the feeding mechanism, port position and the load values are optimized to offer a reading range of about 6-8 inches for a U.S.A standard reader with 4 W EIRP. The 'bare' tag as described above is further optimized by encapsulating it in a radio transparent material that withstands autoclaving. While doing so, a miniature metallic cavity is used in close proximity to the bare tag and within the encapsulation to isolate the effects of metal plane of mounting. The complete tag is designed for optimum performance (within the constraint of physical size) for the entire UHF range, namely 860 to 960 MHz, thereby making the tag global in operation. However, minor modification in the lumped component values can specifically enhance the performance in any particular geography of operation. For instance, use of a range of 902 to 928 MHz will enhance performance in the United States, while to optimize performance in the other geographies like Europe, a range of 865 to 867 MHz is preferred.

Antenna Design

The two antenna designs are presented. These antennas belong to the class of planar antennas that are better known as microstrip antennas. In a standard UHF planar antenna design, the size of the antenna is typically $\lambda/2$, which will be close to 100-150 mm at 1 GHz (considering a dielectric material other than air).

In the present designs, reduction of the size of the antenna below 12 mm, preferably below 9 mm, and more preferably below 7 mm while maintaining a desired impedance match and reading range.

Both the designs presented in this document are variants of standard circular, rectangular, or square microstrip patch antenna; such as in elliptical form or deformed circular shape. Lower frequency resonance (for purpose of excitation) is created by loading the antenna structure by lumped components. A microstrip antenna can be treated as parallel RLC resonator (being leaky cavity). Therefore, an additional loading in the form of any combination of R, L, and C can generate resonance well below the fundamental resonance. Appropriate combination of R, L an C values can be selected for obtaining the best possible impedance match and reading range.

The two designs presented along with their simulated performance (using ANSOFT HFSS) realized gain. In the terminology used by the tool 'HFSS', realized gain of an antenna presents the gain obtained after considering the mismatch loss and the radiation efficiency. Thus 'realized gain' can be directly converted to 'reading range' using equation 1 provided below:

$$R = \frac{\lambda}{4\pi} \sqrt{\frac{P_t G_{reader} G_{tag} \chi}{P_{threshold}}}$$ Equation 1 wherein, $P_t$ is the reader transmitter power and $G_{reader}$ is the antenna gain. For range computation, $P_t G_{reader}$=4 W for the USA and 2 W for Europe. The tag antenna gain $G_{tag}$ is obtained through simulation. The value of $\chi$=0.5 (−3 dB), which is the polarization mismatch loss, if the reader antenna is considered to be circularly polarized. In this case, $P_{threshold}$ is equivalent to −15 dBm.

Antenna and IC Chip Designs

Figure 4A:
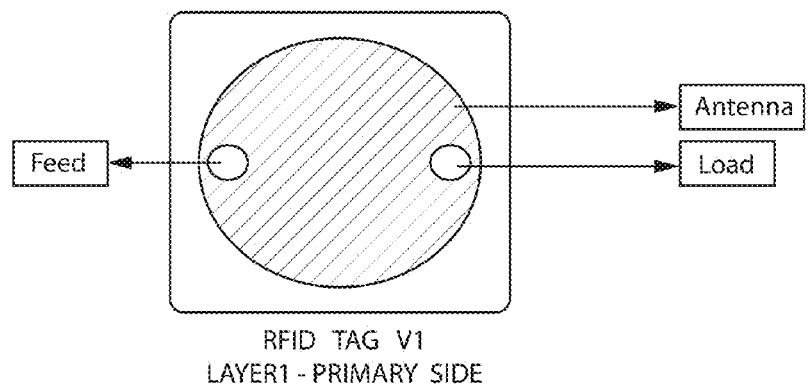
FIG. 4A—Design 1 of the Passive RFID Tag (Top Layer)
FIG. 4B—Design 1 of the Passive RFID Tag (Bottom Layer)
FIG. 4C—Design 2 of the Passive RFID Tag (Top Layer)
FIG. 4D—Design 2 of the Passive RFID Tag (Bottom Layer)
FIG. 5A—Return Loss and Transmission Loss of Design 1
FIG. 5B—Return Loss and Transmission Loss of Design 2
FIG. 6A—Reading Range (mm) versus Elevation Angle for a Given Azimuth Angle at 865 MHz for 2 W EIRP for Design 1
FIG. 6B—Reading Range (mm) versus Elevation Angle for a Given Azimuth Angle at 915 MHz for 4 W EIRP for Design 2
FIG. 7—Three Dimensional Simulated Realized Antenna Gain at 915 MHz (Realized gain includes efficiency and mismatch loss).
Figure 4B:
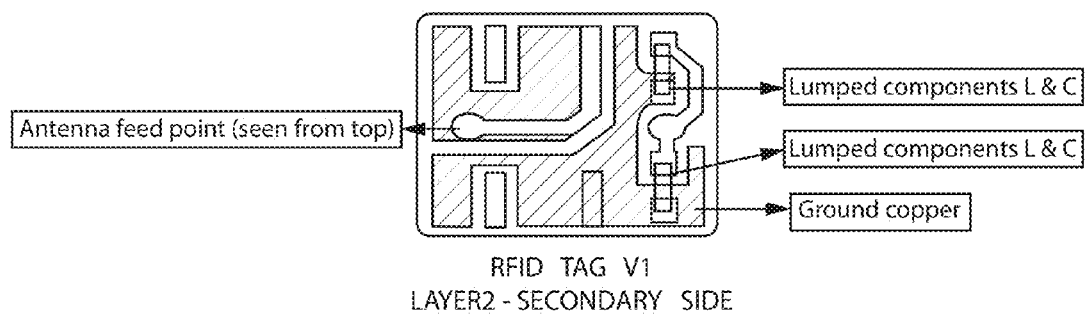

The first chip design is found in FIG. 4A and FIG. 4B. The fundamental resonance is reduced by loading the antenna by a parallel LC circuit, where L=6.8 nH and C=2.2 pf. The antenna can be fine-tuned by varying the value of C, e.g., by using a trimmer capacitor. The following FIG. 4 displays the typical antenna with feed and load. From the chip design in FIG. 4, it was observed that by removing the NC (non-connected) pads, the performance of the tag improved, because of extending the ground copper below the PCB surface. FIG. 4A (Not to scale), displays an antenna Layer having Feed, Antenna, and Load locations, and FIG. 4B displays a bottom layer, showing the pads of the RFID IC having an antenna feed point, lumped components L and C, and a copper ground (Note: the bottom layer is as seen from the top).

Figure 4C:
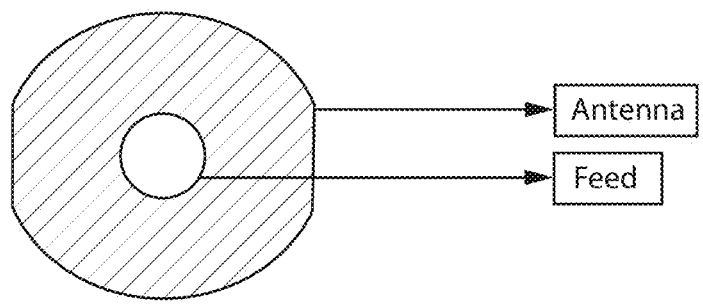
Figure 4D:
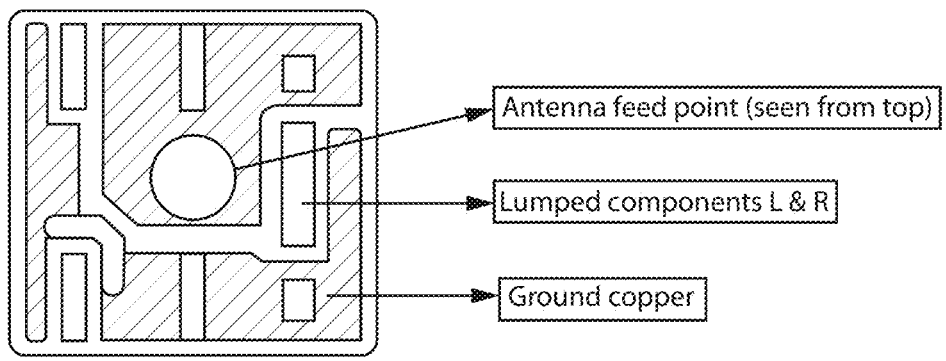

The second chip design is found in FIG. 4C and FIG. 4D, the fundamental resonance is reduced by loading the antenna by an inductor L=12 nH; the impedance matching is then obtained by introducing a low value of resistor R=1_ in series with the inductor. It is to be noted that introduction of a resistor 'R' in the current flowing path dissipates some of the energy, thereby reducing the radiation efficiency. FIG. 4C displays the top layer with the antenna with feed locations. FIG. 4D displays the bottom side with Antenna feed point, Lumped components for L & R, and copper ground. In the second chip design, the RFID IC is excited by the receiving antenna by two methods; namely direct connection using a Plated Thorough Hole (PTH) through the center of the 'deformed circular' patch and secondly by electromagnetic coupling due to the finite thickness and spread of the feeding line below the antenna. The lumped components R & L in series is placed on the bottom layer as displayed in FIG. 4D.

Substrate

The substrate chosen for both first and second chip designs is a Roger's Ultralam (_r=2.5; tan_=0.0015; h=0.483 mm); Double sided Cu Clad.

The Size of the PCB: 6 mm×6 mm×0.483 mm with a Copper thickness on PCB: 0.034 mm Chip Encapsulation and Metallic Plane Both first and second designs for the RFID Tag (FIG. 1. and FIG. 2.) were further processed by encapsulating the dielectric material in Radel® R. Radel® R polyphenylsulfones are natural extensions of Solvay's line of high performance engineering thermoplastics. Radel® R polyphenylsulfone offers exceptional toughness and resistance to impact with even better chemical resistance. Radel® R polyphenylsulfone was suitable for its ultimate toughness with chemical and hydrolysis resistance superior to all commercially available transparent resins or when resistance to commercial autoclave environments is needed. Radel® R polyphenylsulfone is offered in several grades: R-5000, the general purpose transparent grade; R-5100 colors, R-5500, an extrusion grade; and R-5800, a higher flow transparent grade. Radel® R 1000 is processed from R-5500 and extruded in the form of sheet or bar as the encapsulation is placed on carrier. Radel® R was preferred for its toughness and strength for encapsulating the device.

|  | R-5000 | P-5100 NT15 | R-5500 | R-5800 | R-5900 | PPSU 1000 |
|---|---|---|---|---|---|---|
| Specific Gravity | 1.29 | 1.3 | 1.29 | 1.29 | 1.29 | 1.29 |
| Refractive Index | 1.672 | opaque | 1.672 | 1.672 | — | 1.672 |
| Melt Flow at 689° F. (365° C.), 5.0 kg, g/10 min | 17 | 17 | 15.5 | 25 | 30 | — |
| Mold Shrinkage, % | 0.7 | 0.7 | 0.7 | 0.7 | 0.7 | — |
| Steam Sterilization, cycles | >1000 | >1000 | >1000 | >1000 | >1000 | — |
| Water Absorption at 24 hours, % | 0.37 | 0.37 | 0.37 | 0.37 | 0.37 | — |
| Form of availability | Granule | Granule | Granule | Granule | Granule | Sheet/Bar |
| Suitable Manufacturing Process | Injection molding | Injection molding | Extrusion | Injection molding | Injection molding | Machining |

The Radel® R dielectric material chosen for encapsulation was formed as following on the device:

RADEL (Poly Phenyl Sulfone 1000) which having _r=3.5; tan_=0.008

Thickness on top of tag surface: 1 mm

Thickness on four sides of tag surface: 0.7 mm

The encapsulated tag was designed to be in proximity of a metallic plane at a distance of 1.1 mm (below IC) from the tag.

Return Loss and Transmission Loss Indicators

It is observed from the simulation of the encapsulated material resulted in higher performance due to the metallic plane. The performance of tag has improved, because metallic plane acts as a ground plane. The impedance matching and the transmission loss figures are displayed for the first chip design in FIG. 5A and are displayed for the second chip design in FIG. 5B. It is worth noting that the transmission loss occurs when the RFID antenna is irradiated by a plane wave (interrogating signal) from the reader. A better impedance match will allow a maximum power transfer, thereby increasing the reading range.

Figure 5A:
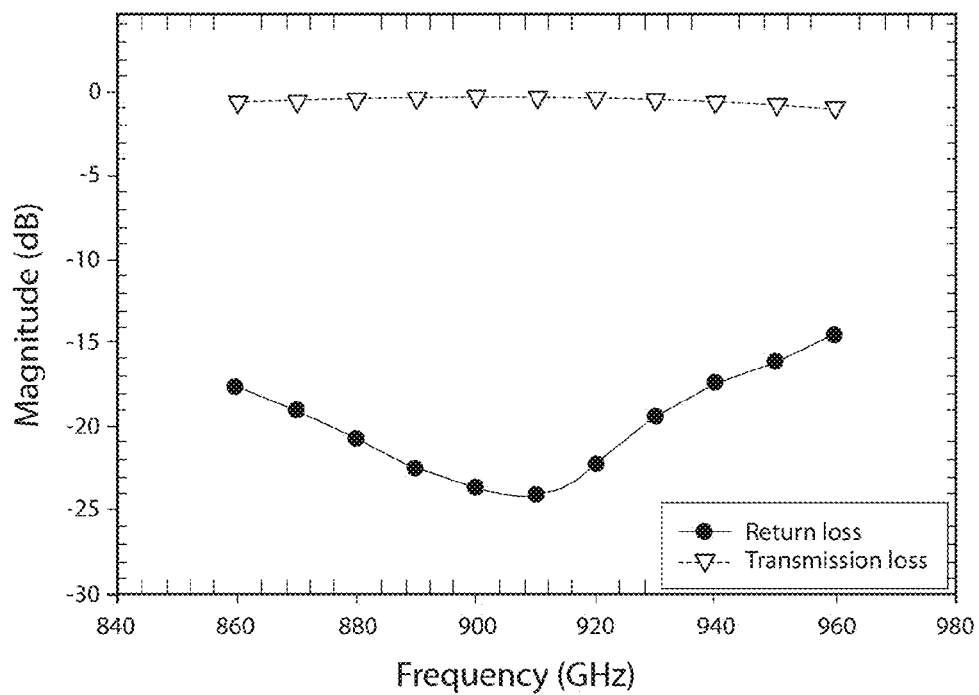

FIG. 5A illustrates that the antenna used in Design 1 is tuned at the frequency band applicable for US standards. However, unlike most of the existing commercial designs, the bandwidth obtained is significantly improved. It was observed from simulation results that by using variable (trimmer) capacitor, the value of capacitor will have to tune between 2.2 pF to 2.7 pF in order to obtain a flatter impedance match.

Figure 5B:
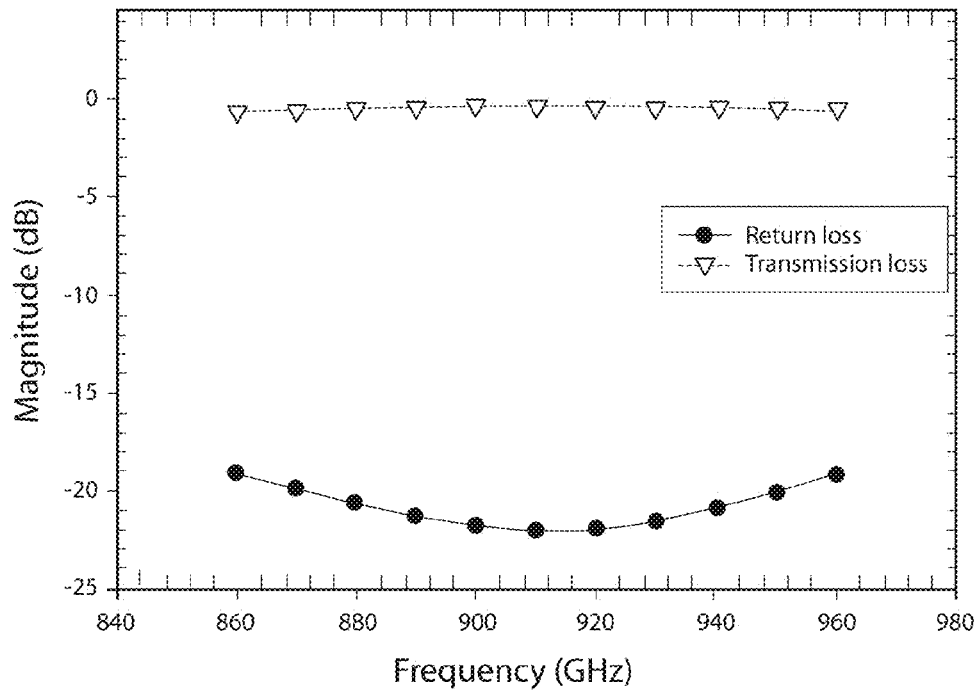

FIG. 5B displays that the antenna of the second design is well matched to the RFID chip. However, the matching figures need to be considered with caution. Small variations in the values of lumped components (even due to percentage tolerance) will degrade the matching, increase the transmission loss, and thereby reduce the projected range. However, even with the possible changes, the reading range will be sufficient to meet USA and European standards.

Reading Range

Both designs were simulated with the RFID tag being encapsulated and having a metallic plane. Performance of both devices was simulated using Electromagnetic simulation tool (ANSOFT HFSS). The simulation results are obtained by using HFSS. The reading range is obtained by using equation 1.

Figure 6A:
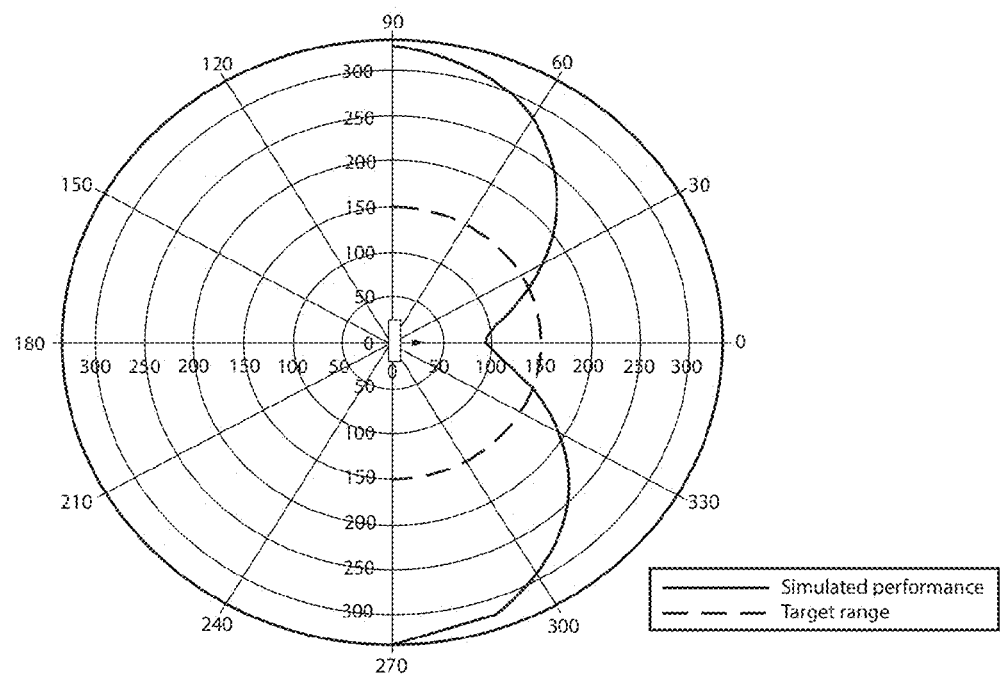
Figure 6B:
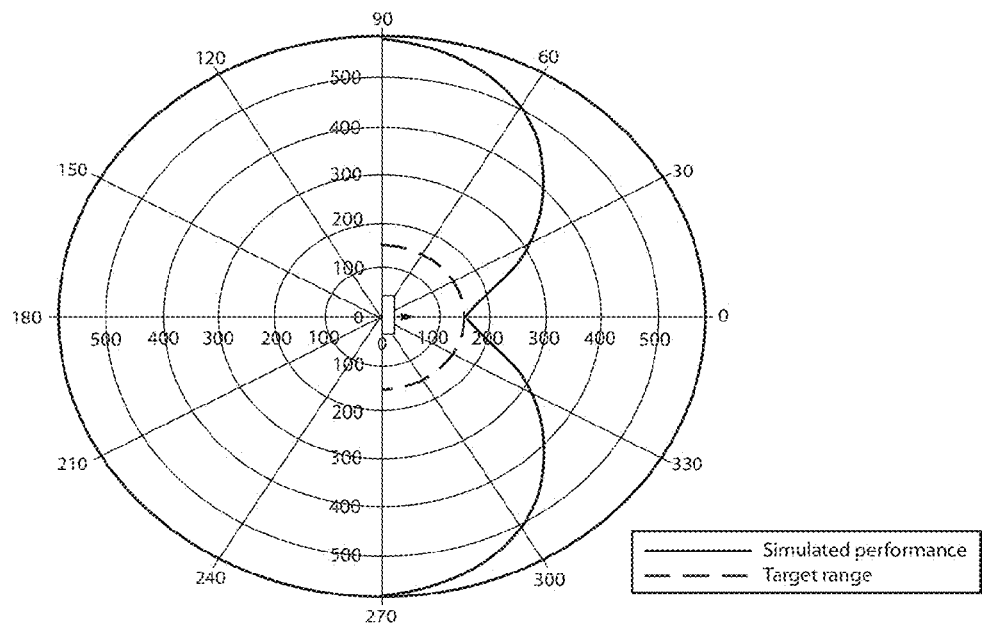

The simulated results for Design 1 is plotted for both the USA standard at 915 MHz in FIG. 6A and for the European standard at 865 MHz in FIG. 6B. A simulated 3-dimensional realized antenna gain at 915 MHz including radiation efficiency and mismatch loss is shown in FIG. 7.

FIG. 6A illustrates the relation of the realized gain for Design 1 (as also shown three dimensionally in FIG. 7) to the reading range possible at 865 MHz (European Standard). The RFID tag far exceeds the requirement of 6" (152.4 mm) for angles beyond 200 on either side. The normal to the antenna face is indicated by an arrow head. The reading range plot for USA standards is plotted in FIG. 6B. The realized gain at 915 MHz is more than 865 MHz. Also the permissible power level is twice the European standard. Thus the present design displays a possibility of much extended range of approximately one and half feet.

Figure 7:
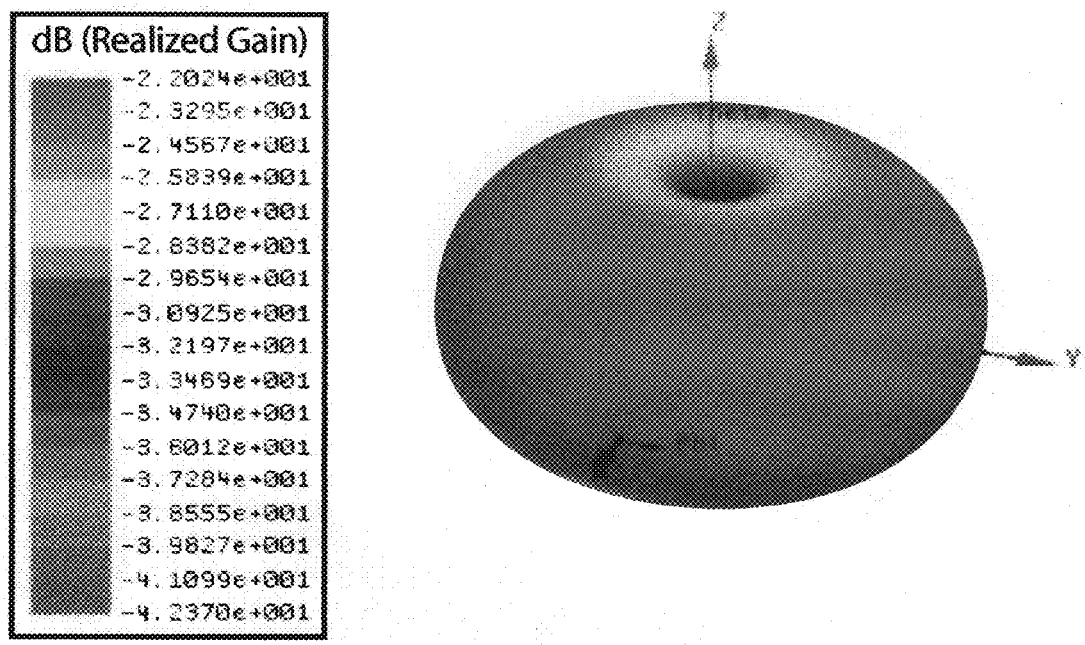

FIG. 7 illustrates for Design 1, a three dimensional simulated realized antenna gain at 915 MHz including radiation efficiency and mismatch loss. The simulated gain of Design 1 shows a dumb-bell like pattern with a defined null normal to antenna. It is to be understood that the simulation assumes an ideal model for some structures (e.g. perfect electric conductor) which deviates in real life. Therefore the null depth will significantly change in real life scenario. The 3D pattern also displays that the tag can be picked up from any direction i.e. 360° on the azimuth plane.

Figure 8A:
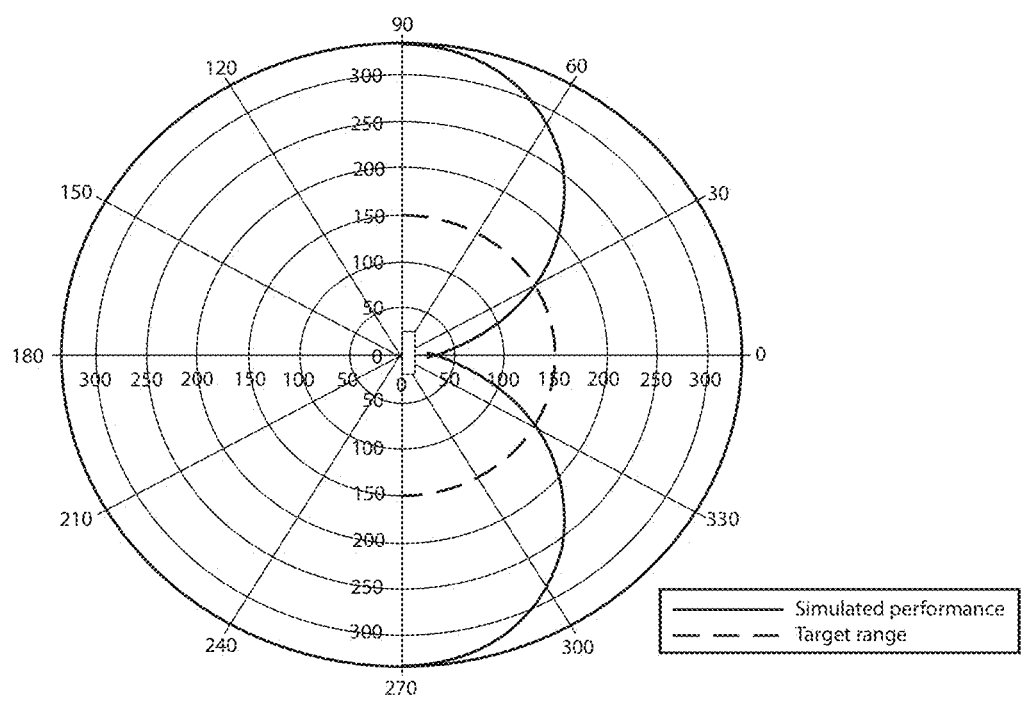
FIG. 8A—Reading Range (mm) versus Elevation Angle for a Given Azimuth Angle at 865 MHz for 2 W EIRP for Design 2
Figure 8B:
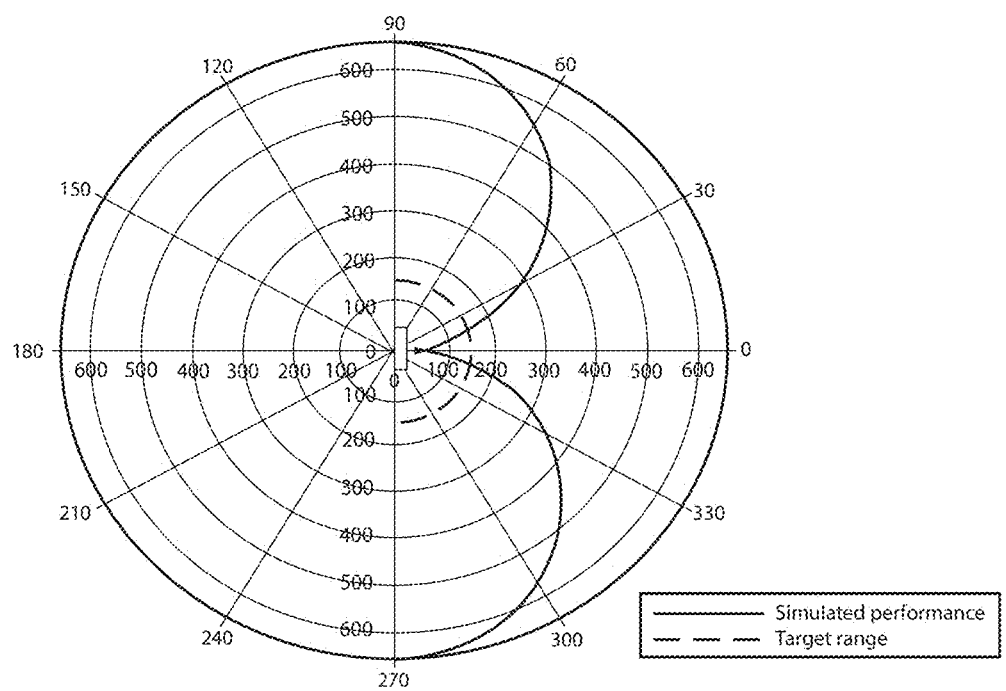
FIG. 8B—Reading Range (mm) versus Elevation Angle for a Given Azimuth Angle at 915 MHz for 4 W EIRP for Design 2

The simulated reading ranges for both European and USA territories are displayed in FIGS. 8A and 8B, respectively. It is important to note that FIGS. 8A and 8B display the reading range for one azimuth angle only. But if we revisit FIG. 7, which displays the pattern in dimensional form for Design 1, one can quickly conclude that the projected range values are applicable for any azimuth angle. The above results are very significant; they demonstrates that the RFID tag is likely to be detected for any orientation on the horizontal plane (assuming that the tag will be placed in a way that the normal direction to the antenna face points toward the ceiling). It also confirms that even when the tag is tilted (with respect to an imaginary vertical line intersecting both the ceiling and the floor), the required range is achievable for most probable situations.

The simulation based results shown above highlight one key feature in small antenna performance. A much reduced (in size) antenna will definitely show a NULL at θ=0° and it cannot be avoided. But in real life applications, the tag antenna will be detected for random orientations most of the time. While Candidate Design 2 shows better promise in terms of performance, Design 1 has an advantage since it can be optimized easily by using a miniature trimmer capacitor (SMD style) instead of a fixed value capacitor in parallel to inductor. Candidate Design 2 is more critical on the tolerance of component values. The simulation based results shown above for Design 1 and Candidate Design 2 were tested in the proximity of metallic plane at distance 1.1 mm from tag surface and with encapsulation consideration. It is observed that due to metallic plane the performance of tag improved.

What is claimed is:

1. A radio frequency identification (RFID) tag, comprising:
a low profile circuit board assembly including:
a circuit board,
RFID integrated circuits, and
a microstrip patch antenna, and
a thin metallic ground plane;
wherein said circuit board having a first side and a second side, said circuit board carrying said microstrip patch antenna on said first side and said ground plane on said second side, said microstrip antenna suitably loaded in shunt by lumped components resistor (R), inductor (L) and capacitor (C), and said RFID circuit being coupled with each of said antenna and said ground plane;
wherein said circuit board assembly is environmentally resistant and autoclavable; and
wherein said RFID tag operates throughout a global UHF frequencies.

2. The RFID Tag of claim 1, wherein micro strip antenna suitably loaded with a fixed value capacitor (C).

3. The RFID Tag of claim 2, where said microstrip patch antenna is capable of specific optimization by use of a trimmer capacitor.

4. The RFID Tag of claim 1, wherein said microstrip patch antenna is capable of specific optimization of the antenna design.

5. The RFID tag of claim 1, wherein said low profile circuit board is less than 11 mm in any unit dimension, or less than 9 mm in any unit dimension, or is less than 7 mm in any unit dimension.

6. The RFID tag of claim 1, wherein said tag size with encapsulation is 11 mm×11 mm or less, or 9 mm×9 mm or less, or 7 mm×7 mm or less.

7. The RFID tag of claim 1, wherein said RFID circuits has 884 bit or larger memory capacity.

8. The RFID tag of claim 1, wherein said RFID circuits has 512 bit or larger user memory.

9. A radio frequency identification (RFID) tag, comprising:
a low profile circuit board assembly including:
a circuit board,
RFID integrated circuits, and
a microstrip patch antenna, and
a thin metallic ground plane;
wherein said circuit board having a first side and a second side, said circuit board carrying said microstrip patch antenna on said first side and said ground plane on said second side, said RFID integrated circuit being coupled with each of said antenna and said ground plane; and
wherein said microstrip patch antenna maintains a complex impedance match over the entire 860 MHz to 960 MHz frequency band.

10. The RFID tag of claim 9, wherein said microstrip patch antenna that has a reading range of about 6 inches.

11. The RFID tag of claim 9, including a backplane coupled with said ground plane.

12. The RFID tag of claim 11, wherein said backplane includes a pair of mounting holes in an area outside said ground plane.

13. The RFID tag of claim 9, wherein said microstrip patch antenna is a folded antenna with an impedance matching stub coupled with said RFID integrated circuit.

14. The RFID tag of claim 9, wherein said ground plane is a copper ground plane.

15. The RFID tag of claim 9, wherein said copper ground plane acts as a shield.

16. The RFID tag of claim 9, wherein said further comprising a housing is comprised of an autoclavable material which can withstand multiple autoclave cycles at a temperature of greater than approximately 250° F.

17. The RFID tag of claim 9, wherein said circuit board carries said RFID circuit on said first side.

18. The RFID tag of claim 17, wherein said RFID integrated circuit includes an integrated circuit (IC) coupled with said antenna.

\* \* \* \* \*